(12) United States Patent
Pichon et al.

(10) Patent No.: US 8,423,117 B2
(45) Date of Patent: Apr. 16, 2013

(54) SYSTEM AND METHOD TO PROCESS AN ACQUIRED IMAGE OF A SUBJECT ANATOMY TO DIFFERENTIATE A PORTION OF SUBJECT ANATOMY TO PROTECT RELATIVE TO A PORTION TO RECEIVE TREATMENT

(75) Inventors: Eric Pichon, Paris (FR); Stephen Solomon, New York, NY (US); George Getrajdman, New York, NY (US); Michel Grimaud, Montrouge (FR); Yves Trousset, Palaiseau (FR)

(73) Assignee: General Electric Company, Schenectady, NY (US)

( * ) Notice: Subject to any disclaimer, the term of this patent is extended or adjusted under 35 U.S.C. 154(b) by 895 days.

(21) Appl. No.: 12/489,138

(22) Filed: Jun. 22, 2009

(65) Prior Publication Data

US 2010/0324407 A1    Dec. 23, 2010

(51) Int. Cl.
*A61B 5/05*    (2006.01)
(52) U.S. Cl.
USPC .................................................. 600/407
(58) Field of Classification Search .......... 600/455, 600/437, 407, 416; 382/195, 131, 132, 128; 358/504
See application file for complete search history.

(56) References Cited

U.S. PATENT DOCUMENTS

| | | | |
|---|---|---|---|
| 5,553,618 A * | 9/1996 | Suzuki et al. | 600/411 |
| 7,421,061 B2 | 9/2008 | Boese | |
| 7,467,007 B2 | 12/2008 | Lothert | |
| 7,613,335 B2 * | 11/2009 | McLennan et al. | 382/128 |
| 2006/0098876 A1 * | 5/2006 | Buscema | 382/195 |
| 2006/0241463 A1 * | 10/2006 | Shau et al. | 600/455 |
| 2007/0247454 A1 | 10/2007 | Rahn et al. | |
| 2007/0263915 A1 * | 11/2007 | Mashiach | 382/130 |
| 2008/0103385 A1 * | 5/2008 | Ma et al. | 600/416 |
| 2008/0125640 A1 * | 5/2008 | Pichon et al. | 600/407 |
| 2008/0240536 A1 | 10/2008 | Soubelet | |
| 2009/0171244 A1 * | 7/2009 | Ning et al. | 600/567 |
| 2009/0216114 A1 | 8/2009 | Gorges | |

* cited by examiner

*Primary Examiner* — Long V. Le
*Assistant Examiner* — Lawrence Laryea
(74) *Attorney, Agent, or Firm* — Fletcher Yoder, P.C.

(57) ABSTRACT

A system and method to process an acquired image to differentiate a portion of subject anatomy to protect relative to a portion of anatomy to receive treatment is provided. The system includes a controller with program instructions to perform the steps of receiving an instruction to indicate a zone interest of the imaged anatomy to protect associated with treatment of the subject anatomy; calculating a first set of image elements associated with a first circulatory network in communication to supply a first zone of interest to treat and not in communication to supply a second zone of interest to protect; calculating a second set of image elements of the acquired image associated with a second circulatory network in communication to supply the second zone of interest to protect; and creating a display that differentiates the second set of image elements from a remainder of the acquired image.

18 Claims, 6 Drawing Sheets

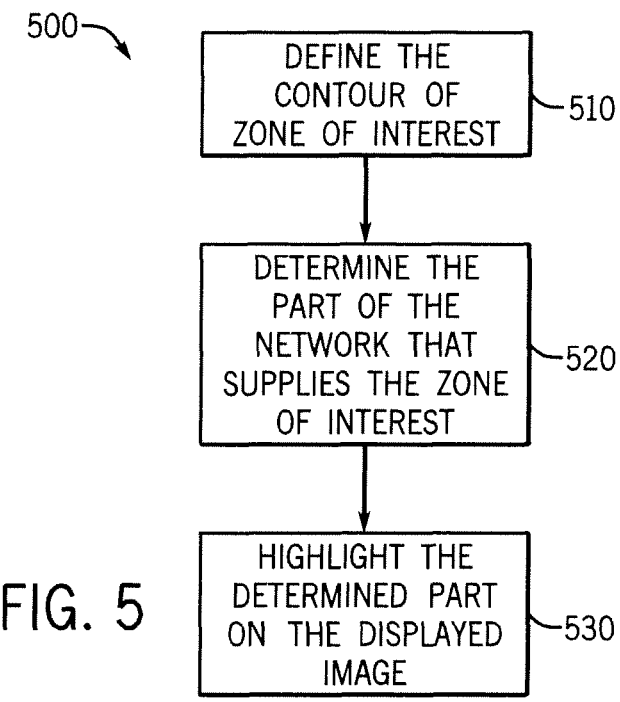
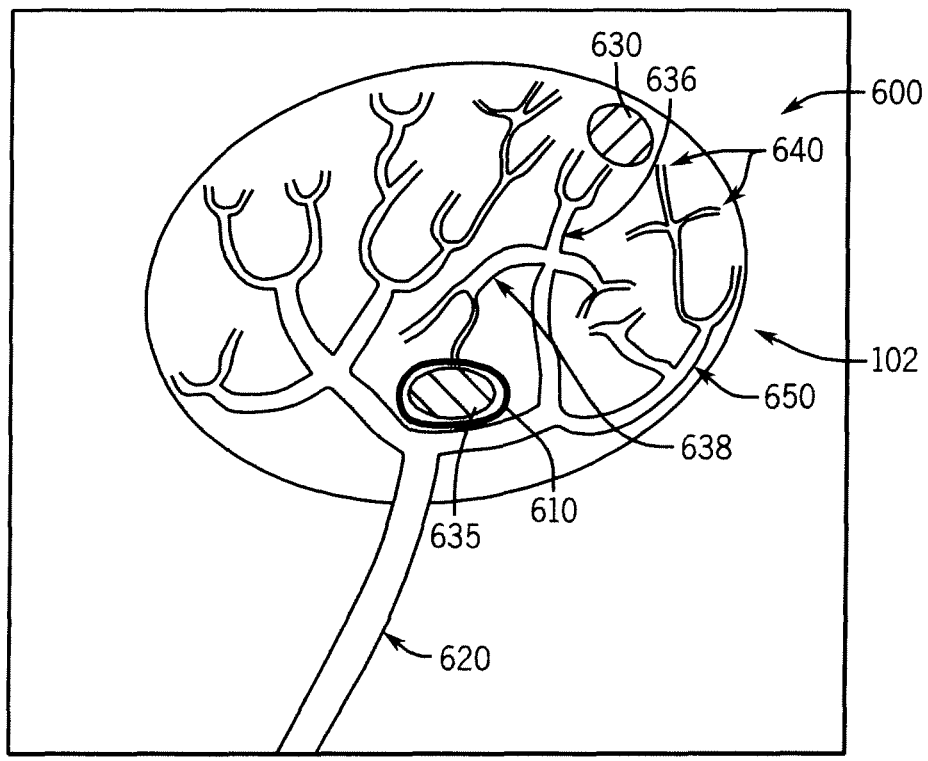

SYSTEM AND METHOD TO PROCESS AN ACQUIRED IMAGE OF A SUBJECT ANATOMY TO DIFFERENTIATE A PORTION OF SUBJECT ANATOMY TO PROTECT RELATIVE TO A PORTION TO RECEIVE TREATMENT

BACKGROUND

The field of the invention relates to the domain of radiology, and more particularly to a system and method to process a radiological image of a body portion in regard to an area to treat or to protect in a circulation network.

Interventional radiology denotes techniques in which a radiologist displays images of a body portion provided by an imagery apparatus to guide or control an operation on this body portion. These techniques are useful for performing operations applied to points of the natural flow or circulation pathways in the body (for example the blood, bile and lymph networks, the airways) in order to treat a target zone of tissue.

For example, the interventional radiologist can introduce a catheter into a vein or artery, or a needle, until reaching a target zone, using an image output by the imagery apparatus. Interventional radiology can be used to treat the target zone of tissue by injecting a substance or by closing off a vessel at a given point in the vascular flow network irrigating the target zone of tissue. In one example, the radiologist can inject ethanol or other drugs to treat a target zone that can include a cancerous tumor. For chemical embolisation, the radiologist can inject an embolic agent and also a toxic substance in a vessel that irrigates the target zone for treatment. The effects of the embolic agent and the toxic substance can combine such that the substance can be concentrated as it is routed to the target zone, and also that blood supply to this zone can be cut off. This described type of treatment enhances focus on the target zone, thus increasing the treatment efficiency while minimizing secondary effects.

To identify and select the target zone for treatment, the radiologist can use of the image output by the imagery apparatus. Interventional radiologists desire to identity and select a target zone that will give an enhanced result in regard to treatment of the target zone, as well as to reduce the impact of the treatment on the surrounding tissues outside the target zone. For example, injecting chemotherapy into the gallbladder when the target zone to be treated is a nearby liver tumor can result in severe abdominal pain.

BRIEF SUMMARY

The system and method of the subject matter described herein can enhance an ability of an interventional radiologist, to identify an optimum operation point in a flow circulation network in order to make a local treatment of a given target zone while reducing or avoiding impact of the treatment in a surrounding tissue outside the target zone.

The subject matter described herein includes an embodiment of a method of processing an acquired image of a body portion intended to receive a treatment associated with a tool, the body portion including a first zone of interest to receive the treatment. The method comprises the steps of receiving an instruction to indicate a second zone interest of the imaged anatomy to avoid impact associated with the treatment; communicating the instruction to a controller; calculating a first set of image elements of the acquired image associated with a first circulatory network in communication to supply the first zone of interest and not in communication to supply the second zone of interest; calculating a second set of image elements of the acquired image associated with a second circulatory network in communication to supply the second zone of interest; and creating a display that differentiates the second set of image elements associated with the second circulatory network from a remainder of the acquired image.

The subject matter described herein also includes an embodiment of a system that comprises an imaging system to acquire an image of a body portion intended to receive a treatment, the body portion including a first zone of interest to receive the treatment; and a controller in communication with the imaging system and a display, the controller including a memory and a processor, the memory including a plurality of program instructions to instruct the processor to perform the steps of: receiving an instruction to indicate a second zone interest of the imaged anatomy to avoid impact associated with the treatment; communicating the instruction to a controller; calculating a first set of image elements of the acquired image associated with a first circulatory network in communication to supply the first zone of interest and not in communication to supply the second zone of interest; calculating a second set of image elements of the acquired image associated with a second circulatory network in communication to supply the second zone of interest; and creating a display that differentiates the second set of image elements associated with the second circulatory network from a remainder of the acquired image.

The embodiment of the method and system of the subject matter described herein can be applicable to a computer readable data storage medium, comprising software instructions for implementing the steps of to process an acquired image of a body portion intended to receive a treatment associated with a tool, the body portion including a first zone of interest to receive the treatment, the plurality of steps comprising: receiving an instruction to indicate a second zone interest of the imaged anatomy to avoid impact associated with the treatment; calculating a first set of image elements of the acquired image associated with a first circulatory network in communication to supply the first zone of interest and not in communication to supply the second zone of interest; calculating a second set of image elements of the acquired image associated with a second circulatory network in communication to supply the second zone of interest; and creating a display that differentiates the second set of image elements associated with the second circulatory network from a remainder of the acquired image.

DESCRIPTION OF THE DRAWINGS

FIG. 5 schematically shows an embodiment of a method of creating an image display that an interventional radiologist would use to examine the vascular network that supplies circulation to a zone of interest to be protected in a body portion.

FIG. 6 schematically illustrates an embodiment of processing an image display employing the method of FIG. 5 and the apparatus of FIG. 1.

DETAILED DESCRIPTION

Figure 1:
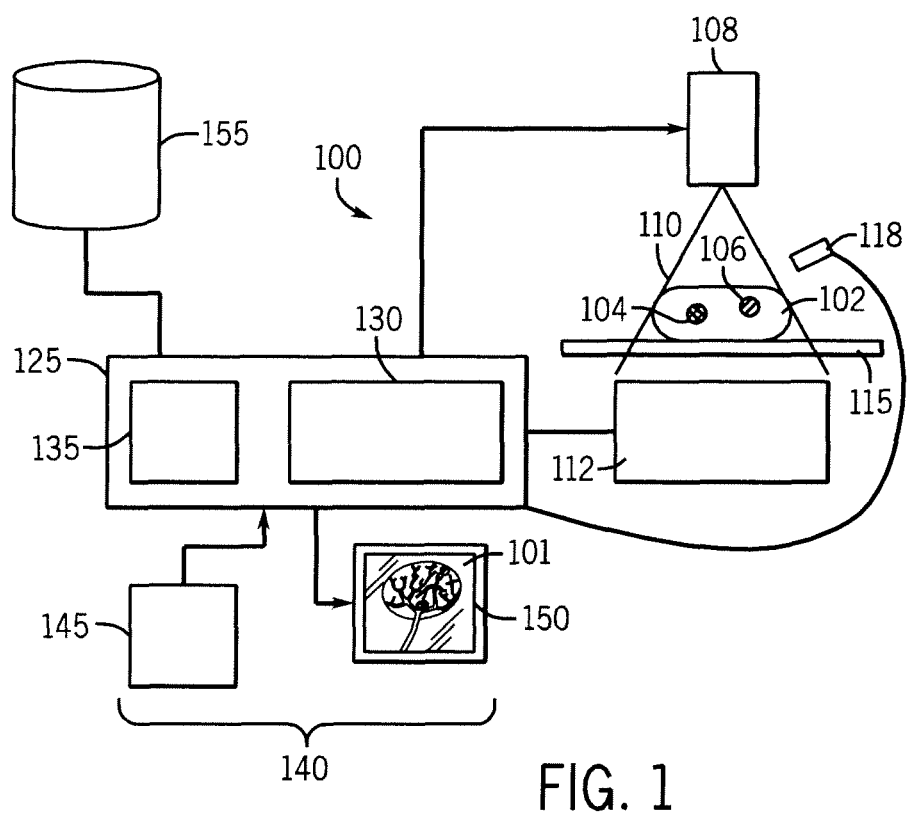
FIG. 1 schematically shows an embodiment of an imaging apparatus.

FIG. 1 shows an embodiment of a system 100 capable to process acquired image or image data 101 of a subject anatomy or body portion 102 so as to differentiate a portion 104 of the subject anatomy 102 to avoid or protect versus a portion 106 of the subject anatomy 102 to receive treatment.

One embodiment of the system 100 is a radiological imaging system that includes a source 108 capable of emitting an X-ray beam 110, a detector 112 placed facing the source 108 and capable of detecting rays emitted by source 108, and a support 115 placed between the source 108 and the detector 112. The support 115 can be configured to receive the subject anatomy 102 (e.g. patient), including for example liver and gallbladder, for which the acquired image 101 is desired. The system 100 can utilize the acquired image 101 to guide a catheter or needle or other tool 118 through the subject anatomy 102. The system 100 can also acquire image data from a picture archival system (PACs) or other type of imaging system.

The system 100 can include a controller 125 (for example a computer) having a processor or processing unit 130 in communication with a memory 135 adapted to receive data supplied by the detector 112 and to control the source 108 and the detector 112. The controller 125 can control the emission of X-rays or source 110110 by the source 108 and the capture of the image 101 by the detector 112. The system 100 can also include an interface 140 having an input 145 (e.g., mouse device, keyboard, touch-screen) and output 150 (e.g., monitor, alarm, etc.). The system 100 can further include a database 155 operable to store the acquired image 101 of the body portion 102.

The controller 125 can be operable to control the interface 140 to display the acquired image data 101 of the subject anatomy 102, where the acquired image data 101 can be acquired in general real-time or can be a pre-recorded in the database 155.

Figure 2:
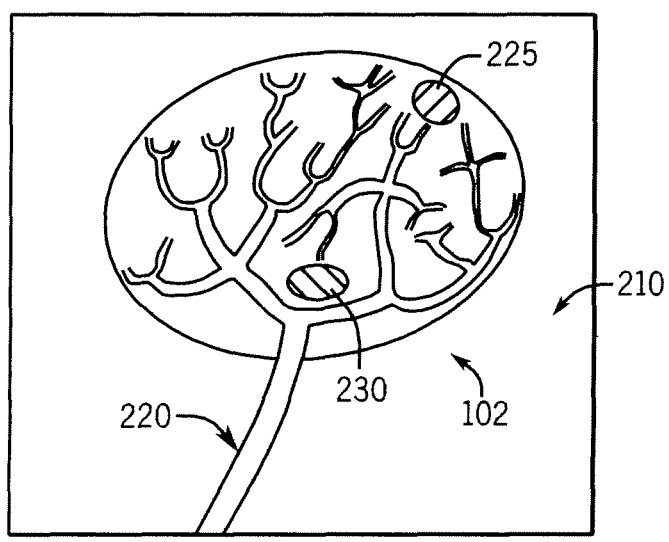
FIG. 2 schematically shows an embodiment of an image of a body portion as it could be obtained using the imaging apparatus according to FIG. 1.

FIG. 2 schematically represents an embodiment of a display 210 illustrative of an acquired image of the subject anatomy or body portion 102 (see FIG. 1) that can be acquired by the system 100 or pre-stored in the database 155 for display on the output 150. The illustrated embodiment of the display 210 can include a three-dimensional composite image resulting from the integration, combination, or overlay of an initial first three-dimensional image of the body portion 102 obtained by X-ray tomography (CT) and an initial second three-dimensional image of the body portion 102 obtained by positron emission tomography (PET). The display 210 of the above-described overlay, combination or fusion of images can be stored in the database 155. In the acquisition of the acquired image data 101, 210, the type (e.g., CT, PET, ultrasound, x-ray, fluoroscopic, magnetic resonance imaging (MRI), etc.) of imaging system 100 or combination thereof can vary.

One embodiment of the display 210 can include data associated with a circulatory network 220 (e.g., vascular that supplies or circulates blood flow) to the body portion 102 (See FIG. 1). The type (e.g., vascular, respiratory, bile, urinary, fecal matter, etc.) of circulatory network 220 can vary. The display 210 can also include an illustration of a zone or region of interest to be treated 225 (e.g., a tumor in the liver) as well as an illustration of a zone or region of interest to be avoided or protected 230 (e.g., gallbladder). The example of the vascular type circulatory network 220 can generally include vessels forming branches connected to each other such that a main branch can provide circulatory blood flow to secondary branches. Assume for sake of example that the region of interest 225 to treat includes or is a tumor in the liver to be treated by operating at a selected operation point or target zone of the vascular network 220, and example of the anatomical region of interest to be avoided or protected 230 is so to reduce or avoid impact (e.g., collateral damage) to the gallbladder.

Figure 3:
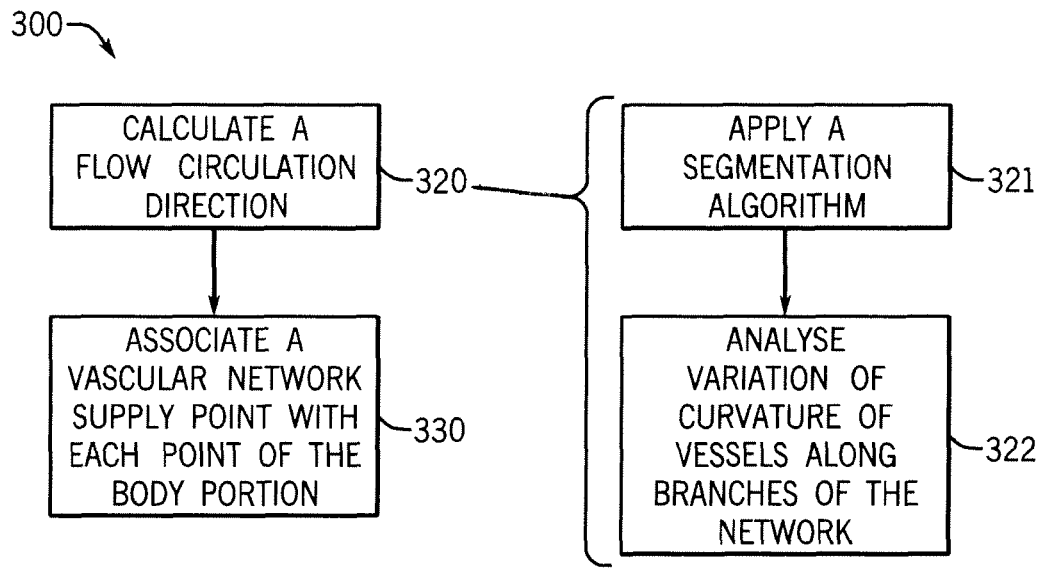
FIG. 3 includes a schematic diagram showing an embodiment of a method of image processing that employs the imaging apparatus of FIG. 1.

FIG. 3 shows a schematic diagram of an embodiment of a method 300 of operating to process acquired image or image data 101 or display 210 of acquired image data of the subject anatomy 102 so as to differentiate the portion 104 of the subject anatomy 102 to avoid or protect versus a portion 106 of the subject anatomy 102 to receive treatment.

Figure 4:
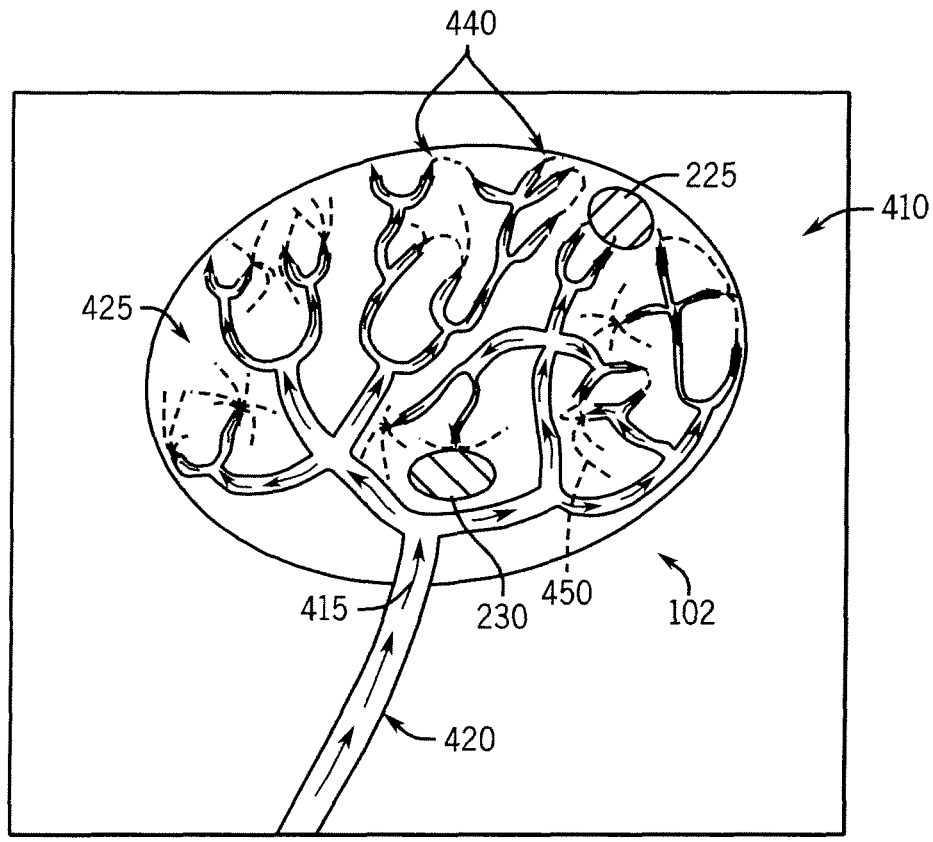
FIG. 4 schematically illustrates an embodiment of processing an image display employing the method of FIG. 3 and the apparatus of FIG. 1.

Referring now to FIGS. 3 and 4, step 320 can include analyzing an acquired image 410 so as to calculate and illustrate a direction of circulation of blood flow (referenced by arrows and reference 415) relative to the acquired image data of the vascular network 420. An embodiment of step 320 can include a step 321 of applying an algorithm to calculate a pattern 425 (including identifying different branches of the structure and direction of circulation 415 associated therewith) of supply, circulation, or irrigation flow in the vascular network 420 in the display 410 of acquired image data.

One example of this type of algorithm can be as described in the "Curve segmentation using directional information, relation to pattern detection" publication, Eric Pichon, Allen Tannenbaum, IEEE International Conference on Image Processing (ICIP), volume 2, pages 794-797, 2005. Step 320 can also include a step 322 of calculating a variation of a radius of a blood vessel of the vascular network 420 along a length of one or more branches of the vascular network 420. An embodiment of the pattern 425 of the supply, circulatory, or irrigation flow direction 415 can be defined according to the direction in which the radius of the vessel structure (e.g., veins, arteries, capillaries, etc.) decreases along the vascular structure, as calculated from the illustration of such vascular structure in the display 410 of acquired image data.

In the display 410 of acquired image data of the body portion 102 (see FIG. 1), step 330 can include identifying one or more terminations or termination points 440 of the vascular network 420. For example, step 330 can include applying an algorithm based on a mathematical model of blood distribution through the tissues of the body portion 102 starting from and creating highlights (shown in dashed lines and by reference 450 in FIG. 4) of image data starting from the vascular network 420 and extending to the termination points 440.

The above-described method 300 can be used to build or create the image 410 to include a map (e.g., irrigation map) of the body portion 102 illustrative of a blood flow circulation, irrigation, or supply direction (see arrows and reference 415 in FIG. 4) in each structural branch of the vascular network 420 and to associate one or several branches with each termination point 440 of the acquired image data of the vascular network 420 of the body portion 102.

FIG. 5 is a schematic diagram illustrative of an embodiment of a method 500 to create or generate displays 600, 700, 800 (See FIGS. 6, 7, 8) illustrative to differentiate a portion of the subject anatomy 102 to treat relative to a portion of the subject anatomy 102 to protect or avoid. Step 510 can include defining a contour 610 (e.g., using a mouse device) in display 600, 700, 800 in the acquired image 101 to delimit one or both zones of interest 630, 635 to treat or to be protected, similar to the acquired image data of the zones of interest 225 and 230 in FIGS. 2 and 4.

Step 520 can include calculating acquired image elements of one or more parts or portions 636, 638 of the network 620 that circulate or supply or irrigate blood flow to the zone of interests 630, 635 to treat or to be protected, respectively. An embodiment of step 520 can include identifying multiple terminations 640 (similar to terminations 400 in FIG. 4) in the blood network 620 contained in the zone of interests 630, 635 to treat or to be protected, and defining or identifying paths 650 initiating therefrom in directions opposite to the direction of blood flow (see arrows and reference 415 in FIG. 4), to calculate the image elements of the parts or portions 636, 638 of the network 620 that supplies, communicates, or irrigates blood flow to the zone of interests 630, 635 to treat or to be protected.

Figure 7:
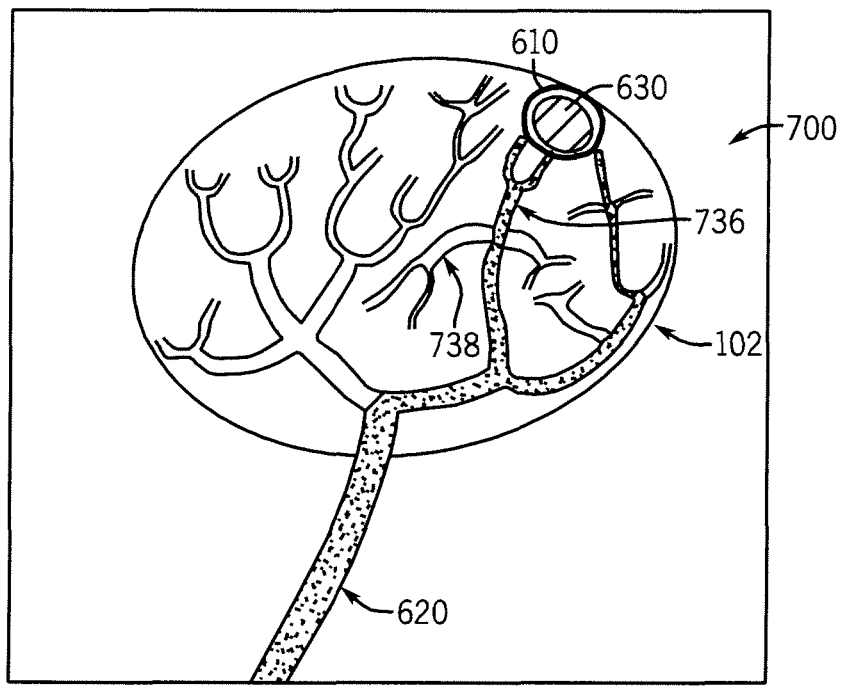
FIG. 7 schematically illustrates an embodiment of processing an image display employing the method of FIG. 5 and the apparatus of FIG. 1.

Referring now to FIGS. 5, 6, and 7, step 530 can include creating highlight graphic representations or highlights of acquired image elements) 736, 738 in the acquired image 700, 800 so as to identify and differentiate the parts or portions 636, 638 of the network 620 (see FIG. 6) from the rest of the image elements of the image 600, 700, 800. An example of the highlights 736, 738 created the highlighting step 530 can include increasing intensity of the pixels associated with the image elements of the parts or portions 636, 638 of the network 620 that supplies, irrigates, or communicates blood flow to the zone of interests 630, 635 to treat or avoid/protect, respectively. Another example of the highlights 736, 738 created in the highlighting step 530 can include applying one color to delineate image elements or data of the parts or portions 636, 638 of the network 620 to differentiate from one another as well as from the remaining image data of the display 700, 800. Another example of the highlights 736, 738 created in step 530 can include variations in or creating transparency of image data of one or more parts or portions 636, 638 of the network 620 to differentiate from one another as well as from the remainder of acquired image 101 of the body portion 102 and/or the display 700, 800.

For example and referring to the display 600 of FIG. 6 to describe the method 500 of FIG. 5, assume the zone of interest 635 to be protected is the gallbladder of an imaged subject. Step 510 can include acquiring input via the input device 145 (see FIG. 1) to define the contour 638 that highlights or differentiates image data of the gallbladder as the zone of interest 635 to be protected. Another embodiment of step 510 can include acquiring input via a stored map of image data, position data, or graphic representation template or combination thereof to create the contour 610 of the zone of interest 635 to be protected, where the stored image data, position data, and/or graphic representation template can be automatically identified from a series thereof based on correlation with acquired data of the medical intervention or procedure or treatment to a particular anatomy to be performed.

Still referring to FIGS. 5 and 6, step 520 can include calculating the image data representative or illustrative of the part or portion 638 (See FIG. 6) of the network 620 that circulates or supplies or irrigates or communicates blood flow to the delimited zone of interest 635 to be protected. This step 520 may only include calculating the image data representative or illustrative of this part or portion 636 to protect or avoid. Referring now to FIG. 7, step 530 can include creating highlights 738 (e.g., color, grey scale level, graphic representation of shading, etc.) of the image data or elements illustrative of the part 636 of the network 620 (See FIG. 6) to protect or avoid so as to differentiate from the acquired image 101 of the body portion 102 and/or the display 700.

Referring to FIGS. 6 and 7 and according to the method 500 of FIG. 5, the highlights 738 differentiate image data of the anatomy of the part 636 of the blood circulation network 620 that circulates or supplies or irrigates blood flow to the zone of interest 635 (e.g., the gall bladder) to be protected or avoided, and such highlights 738 can improve protection of this part 636 of the vascular network 620 from treatment or surgical procedure, which can thereby enhance protection of the zone of interest 635 (e.g., the gallbladder). The system 100 and method 500 also can aid the operator in deciding on one or several operating points or pathways for treatment of a damaged or diseased tissue (e.g., the tumor) by delineating or highlighting the points of the anatomy that can increase opportunities of damages to the zone of interest 635 (e.g., gallbladder) to be protected.

Another example of the system 100 and method 500 can be applied to displays 600 and 700 as illustrated by FIGS. 6 and 7 to identify and highlight the part 636 of the vascular network 620 that supplies, circulates or irrigates blood flow to the zone of interest 630 to be treated. According to this example, step 530 includes creating or generating highlights 736 in the display 700 to differentiate the image data of the part 636 of the network 620 associated with supplying, irrigating, circulating or communicating blood flow to the zone of interest 630 relative to the rest of the image data of the display 700. According to one embodiment, the system 100 can receive via the input device 145 or acquire from memory 135 or database 155 instructions as to a graphic representation template and/or position information or combination thereof that defines image or position data associated with the part 636 of the blood circulation network 620 that participates in supplying, irrigating or circulating blood flow to the zone of interest 630 to be treated. The above-described highlights 736 created by the system 100 and method 500 aid the operator in deciding on one or several anatomical points of the zone of interest 630 (e.g., tumor 12) of the imaged subject 102 for treatment (e.g., surgery, ablation, chemotherapy) and the part 636 of the vascular network 620 that circulates, irrigates or supplies blood flow or other type of flow (e.g., respiratory, bile, feces, urinary, etc.) and/or provides access path(s) 650 (see FIG. 6) to these anatomical points in the zone of interest 630 to be treated.

Figure 8:
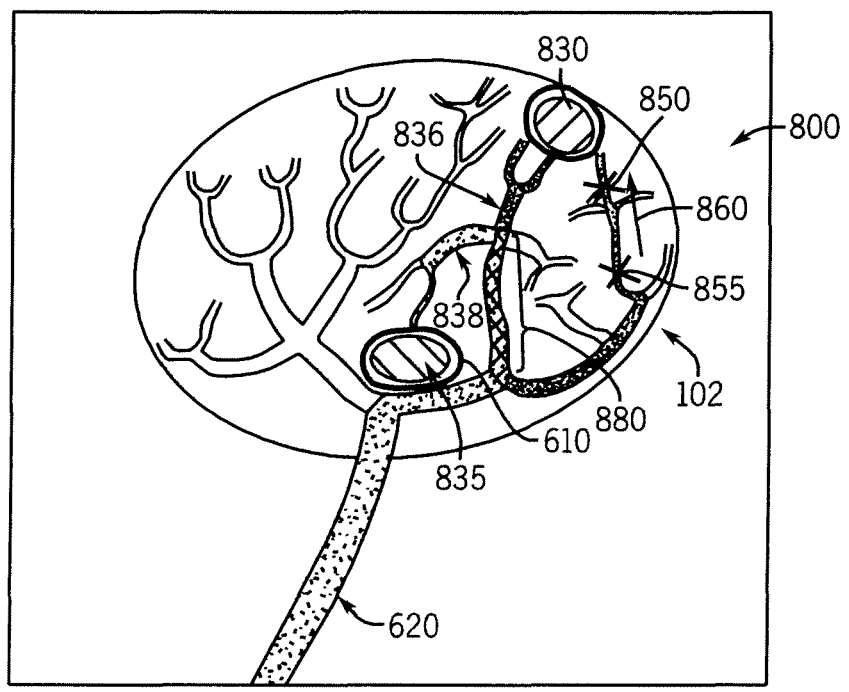
FIG. 8 schematically illustrates an embodiment of processing an image display employing the method of FIG. 5 and the apparatus of FIG. 1.

Referring now to FIG. 8, another embodiment of the highlighting step 530 of method 500 can include creating a display 800 that includes highlighted image elements or data or representation of image data to overlay or fuse with the acquired image 101 (See FIG. 1) of the anatomical zone of interest 630 or 635 to be treated or protected. The step 530 of highlighting of image data or highlighted representation or highlight 836 (shown in light grey) can be calculated to include to differentiate the part or portion 638 (See FIG. 6) of the vascular network 620 to be avoid or protected which supplies, irrigates, or circulates flow to the zone of interest 635 (e.g., gallbladder) to be protected also shown in highlighted representation (shown in dark grey and by reference 835 in FIG. 8), and so as to differentiate from one or more of the representation of the part of the vascular network 21.

The display 800 in FIG. 8 can aid and inform the operator about the localization of the points or part 838 (e.g., represented in light grey) of the circulation network 620 designated be protected and otherwise not submitted to treatment or surgical procedure so as to enhance protection of the zone of interest 835 (e.g., the gallbladder), and further about the localization of the image elements (shown in dark grey) illustrative of the part 836 of the circulation network 620 supplying, irrigating, or communicating flow to the zone of interest 830 (e.g., the tumor and not the gallbladder) to be treated or which a surgical procedure is to be performed.

For example, step 530 of the method 500 can further include identifying and creating highlight or other graphic illustrations of points 850, 855 in the display 800 to guide the tool 118 to perform the medical treatment or procedure. This embodiment of step 530 can include locating the highlights or graphic illustrations of points 850, 855 at or along the part 836 of the circulation network 620 that supplies, irrigates or communicates flow to the zone of interest 830 (e.g., tumor) to be treated, and yet where the part 836 does not irrigate the zone of interest 835 (e.g., gallbladder) to be protected. An embodiment of the controller 125 can propose the path (e.g., illustrated in highlighted or other graphic representation and reference 860) in the display 800 so as to guide the tool 118 (e.g., catheter, needle) to reach the zone of interest 830 for treatment, taking into account the part 838 of the circulation network 620 and the zone 835 to be avoided. The operator can utilize the highlights or graphic illustrations of points 850, 855 on the display 800 to guide the catheter or needle 118 (See FIG. 1) to define the path 860 located along the part 836 of the network 620 that irrigates or circulates flow to the zone of interest 830 (e.g., the tumor) to be treated, and thereby avoid the part 838 so as to better protect reduce opportunities to affect the zone of interest 835 (e.g., gall bladder) to be protected. According to another embodiment, the highlights or other graphic illustration of points 850, 855 can aid the operator in locating injections of substances (e.g., chemotherapy, diagnostics, etc.) via the catheter or needle or tool 118 at in a manner that treats or intervenes (e.g., via circulation or irrigation of foreign substance, ablation, cause very low or high temperature in tissue, etc.) the zone of interest 830 (e.g., the tumor) to be treated, yet with reduced or no effect on the zone of interest 835 (e.g., the gall bladder) to avoid or protect.

An embodiment of step 530 can further include calculating and creating a highlight(s) (shown as a solid line and by reference 880) illustrative of an intersection of the first and second parts 836, 838 of the network 620 to show in combination with the display 800. The embodiment of the highlight 880 illustrative of the intersection can be to isolate and differentiate from the acquired image 101, the rest of the display 800, or from the intersecting parts 836, 838 of the network 620, or combination thereof.

Figure 9:
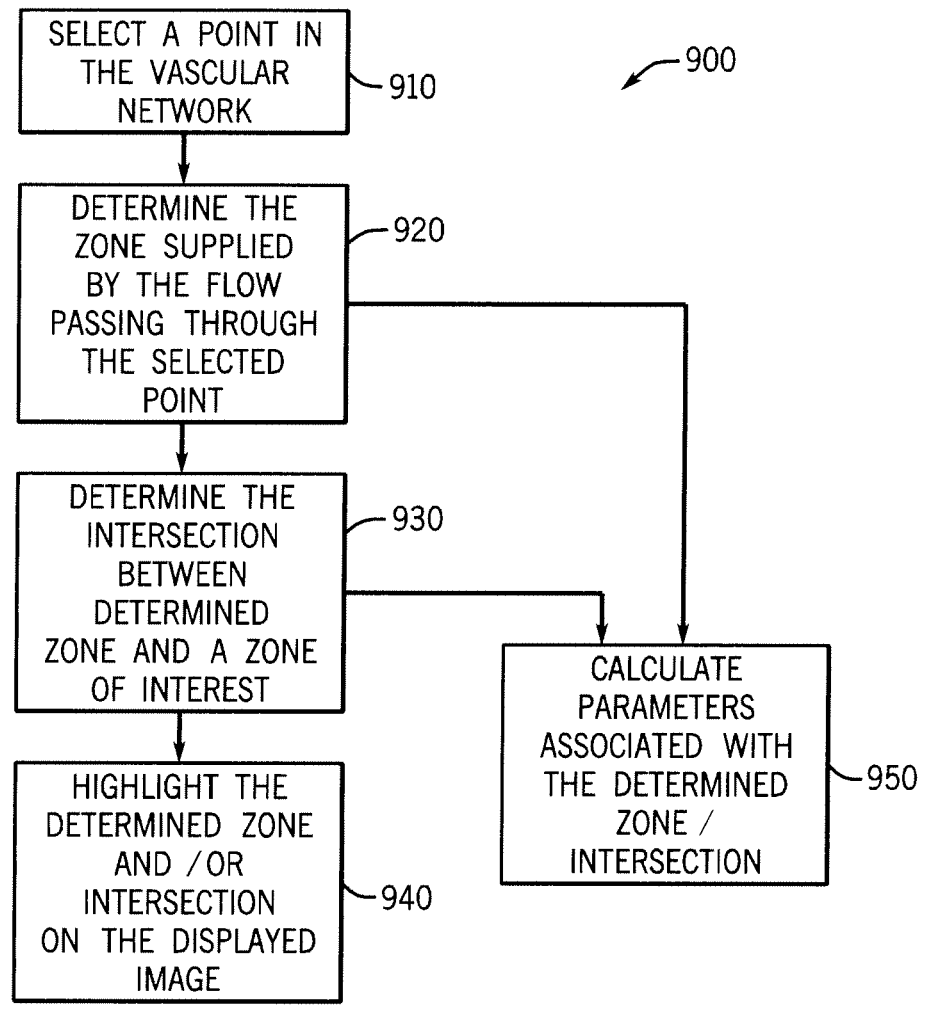
FIG. 9 schematically shows an embodiment of a method of creating a display that an interventional radiologist can use to differentiate a part of a zone to be protected supplied from a point in the vascular network.
Figure 10:
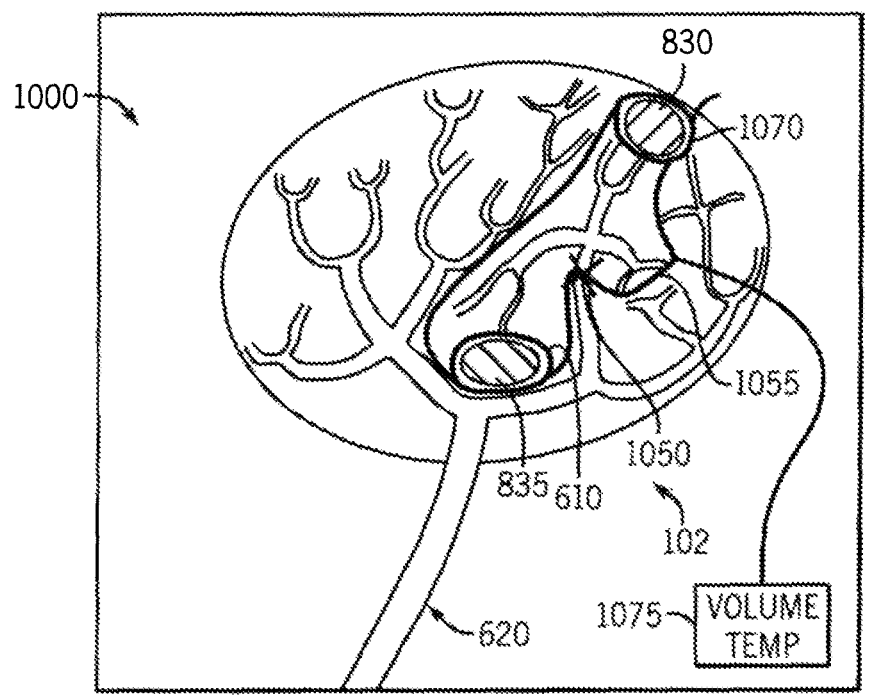
FIG. 10 schematically illustrates an embodiment of creating a display employing the method of FIG. 9 and the apparatus of FIG. 1.

FIGS. 9 and 10 refer to a schematic flow diagram of an embodiment of a method 900 (See FIG. (9) to create a display 1000 (See schematic diagram in FIG. 10) of the zone of interest 830 to treat as a function of a selected point 1050 (e.g., coordinates, pixel, etc.) in the vascular network 620. Step 910 includes acquiring a selection of the point 1050 in the vascular network 620 illustrated in the image 101 (See FIG. 1) via the input device 145 (e.g., the mouse) or from a stored data associated with acquired information of the procedure or treatment to be performed on the particular body portion 102.

Step 920 includes calculating a zone 1055 of the body portion 102 supplied by the blood flow passing through the point 1050. An embodiment of step 920 includes identifying or calculating the branches in the blood circulation network 620 that lie between the selected point 1050 and along vascular structure 620 in the direction of circulation of supply blood flow through point 1050, using techniques as described above. The controller 125 can calculate the zone 1055 of the body portion 102 as that vascular network 620 supplied by the blood flow passing through point 1050 of the vascular network 620.

Step 950 can include calculating measured or calculated parameters (e.g., volume, area, temperature, etc as illustrated in text box and by reference 1075) associated with one or more of the highlight 225, 230, 415, 425, 440, 450, 610, 630, 635, 636, 638, 640, 650, 736, 738, 830, 835, 836, 838, 850, 855, 860, 880, 1050, 1055, 1070 and illustrating these parameters (e.g., by graphic representation such as color, gray scale level, geometric pattern, alphanumeric value, etc.) on one or more displays 210, 410, 600, 700, 800 or 1000.

It should be understood that displays 210, 410, 600, 700, 800, and 1000 are shown by way example. One or more graphic illustrations or highlights 225, 230, 415, 425, 440, 450, 610, 630, 635, 636, 638, 640, 650, 736, 738, 830, 835, 836, 838, 850, 855, 860, 880, 1050, 1055, 1070 created and described shown in one or more displays 210, 410, 600, 700, 800 or 1000 according to one or more steps of the methods 300, 500, and 900 is understood that can be shown in combination with one or more other displays 210, 410, 600, 700, 800 or 1000 or in combination with one or more other methods 300, 500, and 900 and is understood as included as part of the subject matter described herein.

A technical effect of the above-described system 100 and methods 300, 500 and 900 can help the operator check the impact of medical procedures or other treatment on zones of interest to treat as well as zones of interest to avoid or be protected (e.g., the gallbladder) at a given point in the execution of the procedure or treatment as well as any point in acquired image elements of the vascular network 620.

The displays 410, 600, 700, 800 or 1000 can include illustration of the zone of interest 835 (e.g., the part of gallbladder) to be protected and/or of the zone of interest 830 (e.g., tumor) to be treated that may be affected by treatment (e.g., surgical operation, chemotherapy, radiation, heat or cold application, etc.) performed on the selected point 1050 of the imaged anatomy, and can also obtain information about anatomical parameters related to these zones 830 and 835.

Another technical effect of the system 100 and methods 300, 500, and 900 of the subject matter described herein can enhance evaluation of the impact of the treatment of the subject, including the treatment on the zone of interest 835 to be protected and the impact of the treatment on the zone of interest 830 (e.g., the tumor) to be treated.

The memory 135 of the controller 125 can include computer-readable program instructions to instruct the processor 130 to execute one or more of the steps of the methods 300 and 500 described above or combination of steps of method 300 with steps of method 500. It should be understood that the methods 300 and 500 can include additional steps and is not limiting on the subject matter described herein.

The above subject matter has been described with respect to the circulation associated with a vascular network 620 in which blood circulates to supply an organ. Yet, the subject matter is applicable to other types of networks 620 in which fluids circulate in a similar manner, including supply and drain networks, for example such as a bile network, a lymph network, an air circulation network, a urine network, etc. The subject matter may also be applied to other types of networks 620, for example such as a nerve network in which nerve pulses circulate (or propagate) or communicate.

The subject matter described above refers to one zone 835 to be protected or one zone 830 to receive treatment. Yet, it should be understood that the number of zones to protect or treat 830 or 835 can vary.

Also, the subject matter can be applied as well to process other types of zone of interest. For example, zones that received treatment 835 versus zones that have not yet received treatment 830. In another example, zones 830 can be where impact may be avoided versus zones 830 where impact may be observed as a result of treatment. In these example, the system 100 can facilitate and secure the choice of the treatment or avoidance as desired by the user. For example, given the zone of interest 830 as defined by the contour 610 can be the part of the body portion 102 that was previously treated, the methods 300 or 500 or 900 can be performed to illustrate the part of the determined circulatory network 620 supplying the previously treated zone of interest 830 so as to identify and differentiate from the remainder of the acquired image 101 of the body portion 102 or the display 410, 600, 700, 800 or 1000.

This written description uses examples to disclose the subject matter, including the best mode, and also to enable one skilled in the art to make and use the invention. The patentable scope of the subject matter is defined by the following claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method of processing an acquired image of a body portion intended to receive a treatment associated with a tool, the body portion including a first zone of interest to receive the treatment, the method comprising:
    using a processor to perform the steps of:
        receiving an instruction to indicate a second zone of interest of the imaged body portion to avoid impact associated with the treatment;
        identifying a first set of image elements of the acquired image associated with a first part of a circulatory network that circulates flow to the first zone of interest;
    identifying a second set of image elements of the acquired image associated with a second part of the circulatory network that circulates flow to the second zone of interest; and
    creating a display that differentiates the second set of image elements associated with the second part of the circulatory network from a remainder of the acquired image.

2. The method of claim 1, further comprising the step of:
    highlighting the first set of image elements associated with the first part of the circulatory network to differentiate from the remainder of the acquired image.

3. The method of claim 2 further comprising the step of:
    highlighting the second image elements associated with the second part of the circulatory network that circulates flow to the second zone of interest to differentiate the second image elements from the highlighted first image elements as well as the remainder of the acquired image.

4. The method of claim 1, further comprising the step of:
    highlighting acquired image data associated with an intersection of the first part and second part of the circulatory network.

5. The method of claim 1, further comprising the steps of:
    identifying and creating an illustration of at least one point in the acquired image that lies within the first set of image elements associated with the first zone of interest and outside the second set of image elements associated with the second zone of interest; and
    calculating and displaying a path through the illustration of at least one point within the first set of image elements associated with the first zone of interest, wherein the path is displayed to provide a guide for the tool to reach the point to receive medical intervention.

6. The method of claim 1, further comprising the steps of:
    acquiring instructions of limits of a contour that defines a third zone of interest in the acquired image, the third zone of interest corresponding to an already treated portion of the body portion;
    identifying at least a part of the circulatory network that circulates flow to the third zone of interest; and
    highlighting the acquired image data of at least part of the circulatory network associated with the third zone of interest to differentiate from the remainder of the acquired image as to be protected.

7. A system comprising:
    an imaging system to acquire an image of a body portion intended to receive a treatment, the body portion including a first zone of interest to receive the treatment; and
    a controller in communication with the imaging system and a display, the controller including a memory and a processor, the memory including a plurality of program instructions to instruct the processor to perform the steps of:
        receiving an instruction to indicate a second zone of interest of the imaged body portion to avoid impact associated with the treatment;
        identifying a first set of image elements of the acquired image associated with a first part of a circulatory network that circulates flow to the first zone of interest;
        identifying a second set of image elements of the acquired image associated with a second part of the circulatory network that circulates flow to the second zone of interest; and
        creating a display that differentiates the second set of image elements associated with the second part of the circulatory network from a remainder of the acquired image.

8. The system of claim 7, further comprising program instructions to instruct the processor to perform the step of: highlighting the first set of image elements associated with the first part of the circulatory network to differentiate from the remainder of the acquired image.

9. The system of claim 8, further comprising program instructions to instruct the processor to perform the step of:
    highlighting the second image elements associated with the second part of the circulatory network that circulates flow to the second zone of interest to differentiate the second image elements from the highlighted first image elements as well as the remainder of the acquired image.

10. The system of claim 7, further comprising program instructions to instruct the processor to perform the step of:
    highlighting acquired image data associated with identifying an intersection of the first part and second part of the circulatory network.

11. The system of claim 7, further comprising program instructions to instruct the processor to perform the steps of:
    identifying and creating an illustration of at least one point in the acquired image that lies within the first set of image elements associated with the first zone of interest and outside the second set of image elements associated with the second zone of interest, and calculating and displaying a path through the illustration of at least one point within the first set of image elements associated with the first zone of interest, wherein the path is displayed to provide a guide for the tool to reach the point to receive medical intervention.

12. The system of claim 7, further comprising program instructions to instruct the processor to perform the steps of:

acquiring instructions of limits of a contour that defines a third zone of interest in the acquired image, the third zone of interest corresponding to an already treated portion of the body portion;

identifying at least a part of the circulatory network that circulates flow to the third zone of interest, and highlighting the acquired image data of at least part of the circulatory network associated with the third zone of interest to differentiate from the remainder of the acquired image as to be protected.

13. A non-transitory computer readable storage medium comprising a plurality of computer-readable program instructions to instruct a processor to execute a plurality of steps to process an acquired image of a body portion intended to receive a treatment associated with a tool, the body portion including a first zone of interest to receive the treatment, the plurality of steps comprising:

receiving an instruction to indicate a second zone of interest of the imaged body portion to avoid impact associated with the treatment;

identifying a first set of image elements of the acquired image associated with a first part of a circulatory network that circulates flow to the first zone of interest;

identifying a second set of image elements of the acquired image associated with a second part of the circulatory network that circulates flow to the second zone of interest; and creating a display that differentiates the second set of image elements associated with the second part of the circulatory network from a remainder of the acquired image.

14. The non-transitory computer readable storage medium of claim 13, further comprising program instructions to instruct the processor to execute the step of:

highlighting the first set of image elements associated with the first part of the circulatory network to differentiate from the remainder of the acquired image.

15. The non-transitory computer readable storage medium of claim 14, further comprising program instructions to instruct the processor to execute the step of:

highlighting the second image elements associated with the second part of the circulatory network that circulates flow to the second zone of interest to differentiate the second image elements from the highlighted first image elements as well as the remainder of the acquired image.

16. The non-transitory computer readable storage medium of claim 13, further comprising program instructions to instruct the processor to perform the step of:

highlighting acquired image data associated with identifying an intersection of the first part and second part of the circulatory network.

17. The non-transitory computer readable storage medium of claim 13, further comprising program instructions to instruct the processor to execute the steps of:

identifying and creating an illustration of at least one point in the acquired image that lies within the first set of image elements associated with the first zone of interest and outside the second set of image elements associated with the second zone of interest; and calculating and displaying a path through the illustration of at least one point within the first set of image elements associated with the first zone of interest, wherein the path is displayed to provide a guide for the tool to reach the point to receive medical intervention.

18. The non-transitory computer readable storage medium of claim 13, further comprising program instructions to instruct the processor to execute the steps of:

acquiring instructions of limits of a contour that defines a third zone of interest in the acquired image, the third zone of interest corresponding to an already treated portion of the body portion;

identifying at least a part of the circulatory network that circulates flow to the third zone of interest; and highlighting the acquired image data of at least part of the circulatory network associated with the third zone of interest to differentiate from the remainder of the acquired image as to be protected.

* * * * *